(12) United States Patent
Matthis et al.

(10) Patent No.: US 8,262,704 B2
(45) Date of Patent: Sep. 11, 2012

(54) RECEIVING PART FOR CONNECTING A SHANK OF A BONE ANCHORING ELEMENT TO A ROD AND BONE ANCHORING DEVICE WITH SUCH A RECEIVING PART

(75) Inventors: Wilfried Matthis, Weisweil (DE); Lutz Biedermann, VS-Fillingen (DE)

(73) Assignee: Biedermann Technologies GmbH & Co. kG, Donaueschingen (DE)

( * ) Notice: Subject to any disclaimer, the term of this patent is extended or adjusted under 35 U.S.C. 154(b) by 766 days.

(21) Appl. No.: 11/440,489

(22) Filed: May 24, 2006

(65) Prior Publication Data

US 2006/0293666 A1 Dec. 28, 2006

Related U.S. Application Data

(60) Provisional application No. 60/685,798, filed on May 31, 2005.

(30) Foreign Application Priority Data

May 27, 2005 (EP) ..................................... 05011438

(51) Int. Cl.
*A61B 17/70* (2006.01)
(52) U.S. Cl. ........................................................ 606/264
(58) Field of Classification Search .................. 606/246, 606/250, 264, 265, 266, 267, 270
See application file for complete search history.

(56) References Cited

U.S. PATENT DOCUMENTS

| | | | |
|---|---|---|---|
| 5,005,562 A | 4/1991 | Cotrel | |
| 5,443,467 A | 8/1995 | Biedermann et al. | |
| 5,944,720 A | 8/1999 | Lipton | |
| 6,053,917 A * | 4/2000 | Sherman et al. | 606/270 |
| 6,074,393 A | 6/2000 | Sitoto | |

(Continued)

FOREIGN PATENT DOCUMENTS

DE 43 30 837 A1 3/1995

(Continued)

OTHER PUBLICATIONS

European Search Report and Opinion for counterpart European Patent Application EP 05 011 438.8 dated Nov. 2, 2005, 7 pages.

(Continued)

*Primary Examiner* — Eduardo C Robert
*Assistant Examiner* — James Palmer
(74) *Attorney, Agent, or Firm* — Christie, Parker & Hale, LLP

(57) ABSTRACT

A receiving part for connecting a shank of a bone anchoring element to a rod. The receiving part has a first end, a second end and a recess having a substantially U-shaped cross section. The recess extends from the first end in a direction of the second end forming two legs open at the first end. The recess defines a channel to receive the rod. The channel has a longitudinal axis. The legs have an inner thread to receive a securing element having an outer thread cooperating with the inner thread. The legs are provided with stiffening structures. In one embodiment, the stiffening structures are formed by the wall thickness of the outer edges of the legs being larger than the wall thickness of the legs at a location closest to the central axis of the receiving part.

23 Claims, 7 Drawing Sheets

U.S. PATENT DOCUMENTS

| | | | |
|---|---|---|---|
| 6,139,549 A | 10/2000 | Keller | |
| 6,158,437 A * | 12/2000 | Vagley | 128/898 |
| 6,296,642 B1 | 10/2001 | Morrison et al. | |
| 6,302,888 B1 * | 10/2001 | Mellinger et al. | 606/270 |
| 6,884,244 B1 * | 4/2005 | Jackson | 606/306 |
| 7,611,518 B2 | 11/2009 | Walder et al. | |
| 7,833,250 B2 * | 11/2010 | Jackson | 606/270 |
| 2002/0035366 A1 | 3/2002 | Walder et al. | |
| 2002/0133154 A1 * | 9/2002 | Saint Martin | 606/61 |
| 2002/0138076 A1 | 9/2002 | Biedermann et al. | |
| 2003/0100896 A1 | 5/2003 | Biedermann et al. | |
| 2004/0122425 A1 | 6/2004 | Suzuki et al. | |

FOREIGN PATENT DOCUMENTS

| | | |
|---|---|---|
| EP | 0 614 649 A1 | 9/1994 |
| JP | 10-52440 A | 2/1998 |
| JP | 2002-125980 A | 5/2002 |
| JP | 2004-97705 A | 4/2004 |
| WO | WO 03/088856 A1 | 10/2003 |
| WO | WO 2005/041799 A1 | 5/2005 |

OTHER PUBLICATIONS

Extended European Search Report for parallel European Patent Application No. EP 09 00 4848 dated Jul. 2, 2009, 6 pages.

* cited by examiner

RECEIVING PART FOR CONNECTING A SHANK OF A BONE ANCHORING ELEMENT TO A ROD AND BONE ANCHORING DEVICE WITH SUCH A RECEIVING PART

CROSS-REFERENCE TO RELATED APPLICATION(S)

This application claims the benefit of U.S. Provisional Application No. 60/685,798 filed May 31, 2005 and claims the priority of European Patent Application No. 05 011 438.8, filed May 27, 2005, the entire contents of which are both incorporated herein by reference.

BACKGROUND

The invention relates to a receiving part for connecting a shank of a bone anchoring element to a rod and to a bone anchoring device with such a receiving part to be used in spinal surgery or trauma surgery.

A known polyaxial bone screw 100 is shown in FIG. 11. It comprises a receiving part 101 for connecting a screw element 102 to a rod 103, the outer wall of the receiving part being substantially cylindrical. The receiving part 101 has a recess 104 with a substantially U-shaped cross-section forming two open legs 105, 106 defining a channel for inserting the rod 103. An inner thread 107 is provided at said legs for receiving a securing screw 108 to fix said rod in the channel. The inner thread 107 is a metric thread.

When screwing in the securing screw 108 as shown in FIG. 13, forces directed radially outwards which are depicted by arrows A act on said inner thread which cause said legs 105, 106 to splay. This may loosen the fixation of the rod.

Several approaches have been made so far to solve the problem of the splaying of the legs. One solution is to provide tube-shaped counter-holding tools. Another solution consists in providing an outer nut to be screwed onto an outer thread of said legs as, for example, disclosed in EP 0 614 649 A. Also, outer ring-shaped securing means are known. However, securing means such as outer nuts or rings enlarge the size of the bone screw and therefore limit the clinical applications.

A further approach consists in using a specific kind of thread shape for the inner thread 107 and the corresponding thread of the securing screw. It is known to use a saw tooth thread as disclosed in U.S. Pat. No. 5,005,562 or a reverse angle thread such as disclosed in U.S. Pat. No. 6,296,642 B1 or US 2002/0138076 A1 to eliminate the outwardly directed radial forces acting on said legs. A particularly advantageous thread shape is the flat thread as disclosed in US 2003/0100896 A1 which eliminates such radial forces and is easy to manufacture. The use of these specific thread shapes allows a use of the bone screw without a further outer securing device such as an outer nut or ring.

However, despite the above measures there is still a problem of a diagonal splaying of the legs at the time of final tightening of the securing screw. This splaying is caused mainly by the torque acting on said legs 105, 106 at the time of final tightening which causes a diagonal lateral deformation of the open ends of the legs in the longitudinal direction of the rod due to the friction between the thread flanks. The torque B acting on the legs is shown in FIG. 2. The deformation is shown in FIG. 14 which does not show the securing screw for the purpose of better illustration. The problem of the splaying of the legs is not restricted to polyaxial bone screws but also occurs in all so called top open bone anchoring devices including monoaxial screws which have two open legs and a slit in between for inserting the rod.

Providing flattened surfaces 109 at the sides of the receiving part which are oriented in a transverse direction of the channel, as shown in FIG. 12, does not solve the problem but contributes to minimize the size of the bone screw in a longitudinal direction of the rod.

SUMMARY

It is an object of the invention to provide a receiving part, in particular for a polyaxial bone anchoring device, and a bone anchoring device which is connected to a rod which is safe in use and at the same time has a compact design. Further it is an object to provide a tool for holding and/or guiding such a bone anchoring device.

The receiving part according to the invention has the advantage that it prevents or significantly reduces splaying of the legs without using any outer securing means. It is of a reduced size in a direction parallel to the longitudinal axis of said rod. Therefore it is more compact than the known screws. When designing it with the same size as a conventional screw in a direction parallel to the longitudinal axis of the rod, a rod with a larger diameter compared to that of the conventional screw can be used.

Further features and advantages of the invention will become apparent from the description of the embodiments using the drawings.

DETAILED DESCRIPTION

Figure 1:
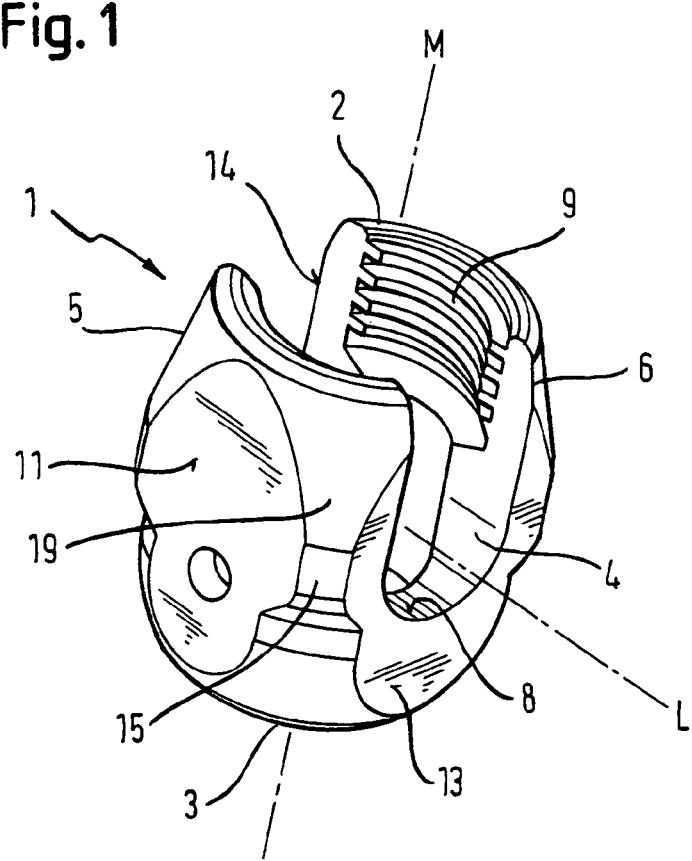
FIG. 1 shows a perspective view of a receiving part according to a first embodiment of the invention.

As shown in FIGS. 1 to 3b a receiving part 1 for connecting a shank 50 of a bone anchoring element 51 to a rod according to the invention comprises a first end 2 and a second end 3, a central axis M and a recess 4 having a substantially U-shaped cross-section. The recess 4 extends from the first end 2 towards the second end 3 and forms two legs 5, 6 open at the first end 2. The recess defines a channel having a longitudinal axis L for the insertion of a rod 7. The longitudinal axis L corresponds to the longitudinal axis of the rod when the rod is inserted. The width of the recess 4 is just as large that the rod can be placed in and fit into the bottom 8 of the recess while still being able to perform a sliding motion in the recess when it is not fixed. The legs 5, 6 project above the rod when the rod is inserted and have an inner thread 9 extending from a position adjacent to the first end 2 in a direction of the second end 3 over a predetermined length to allow a securing screw 10 to be screwed in to fix the rod. The inner thread 9 and the matching outer thread of the securing screw is preferably a flat thread, the upper and lower flanks of which each include an angle of 90 degrees with the screw axis.

At the outer wall surface of the legs 5, 6 two opposite flat surfaces 11, 12 are provided which extend parallel to the longitudinal axis L of the channel and parallel to the central axis M of the receiving part. The flat surfaces 11, 12 are parallel to each other and extend from a first position near the first end 2 to a second position towards the second end 3 which is located below the bottom 8 of the recess 4. Hence, the flat surfaces 11, 12 extend along the portions of said legs which enclose the rod from both sides. The receiving part 1 further comprises at its sides transverse to the longitudinal axis L of the recess two opposite flat surfaces 13, 14 extending from a distance from the first end 2 to a position below the bottom 8 of the recess. The flat surfaces 13, 14 are parallel to the central axis M and to each other. In this way, the flat surfaces 11, 12 and the flat surfaces 13, 14 include an angle of 90°, respectively. In the embodiment shown, the width W of the flat surfaces 11, 12, 13 and 14 in a direction perpendicular to the central axis M is the same so that an envelope E in a circumferential direction of the receiving part near the bottom 8 of the recess is substantially square shaped.

Figure 2:
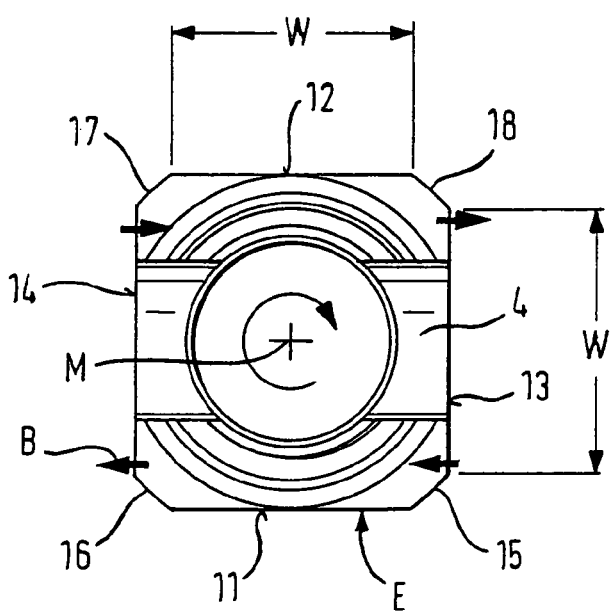
FIG. 2 shows a top view of the receiving part according to the first embodiment.

At the lateral edges of the legs 5, 6 portions 15, 16, 17, 18 with enhanced wall thickness compared to the wall thickness of the legs in the region of the flat surfaces 11, 12 are provided. These portions form stiffening structures preventing or significantly reducing a bending of the legs due to a diagonal splaying. The portions 15, 16, 17, 18 having the enhanced wall thickness have either a flattened outer surface as shown in FIGS. 1 and 2 or a rounded surface. They may extend along the whole length of the flat surfaces 11, 12, 13 or 14 or, as shown in FIGS. 1 and 2, go over in slanted portions 19 with diminishing wall thickness towards the first end 2.

Figure 3A:
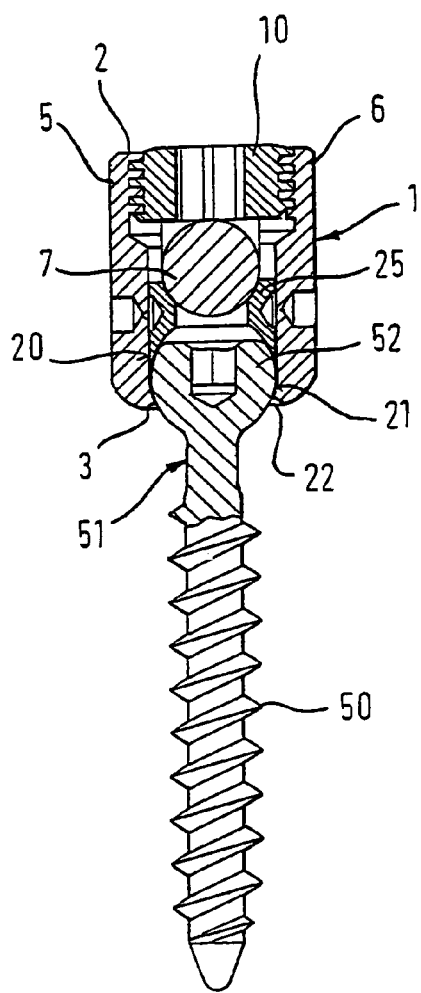
FIG. 3a shows a sectional view of the bone anchoring device with the receiving part of the first embodiment.
Figure 3B:
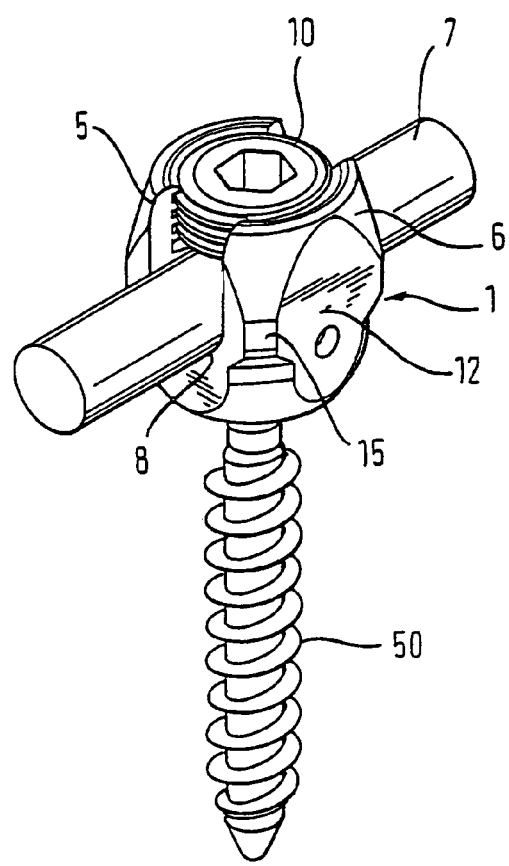
FIG. 3b shows a perspective view of the bone anchoring device with the receiving part of the first embodiment.

FIGS. 3a and 3b show the receiving part according to the invention together with a bone screw 51 to form a polyaxial bone anchoring device. In this case the receiving part 1 further comprises, as shown in FIG. 3a, a coaxial bore 20 extending through the bottom 8 of the channel and tapering in a section 21 towards the second end 3 to provide an opening 22 in the second end 3 which has a diameter smaller than that of the bore 20. The diameter of said bore 20 is larger than the diameter of a head 52 of the screw element 51 to allow the shank 50 and the screw head 52 of the bone anchoring screw 51 to be guided through said bore. The diameter of the opening 22 is smaller than the diameter of the screw head 52 but larger than the diameter of the shank 50. Thus, the tapering section 21 and the screw head 52 form a ball and socket joint to flexibly connect the bone anchoring screw and the receiving part.

A pressure element 25 is provided which is slidable in the bore 20 and serves for exerting pressure on the head to fix the screw element in an angular position with respect to the receiving part when the pressure element is pressed against the head. The pressure element may be substantially disc shaped and may have a recess for encompassing the upper part of the screw head and a recess for accommodating the lower side of the rod 7. The pressure element may also have an opening for allowing a screwing-in tool to be guided through.

As can be seen from FIG. 3b the portion 15 of the receiving part and corresponding portions 16, 17, 18, which have the enhanced wall thickness, are located approximately at the height of the longitudinal axis of the rod when the rod is inserted into the receiving part and the flat surfaces 11, 12, 13, 14 extend over the area where the rod is enclosed by the legs 5, 6 from both sides.

In operation the screw element and the pressure element are inserted into the receiving part. Then the rod is placed in and fixed by means of the securing screw. In the embodiment shown the rod presses on the pressure element when the inner screw is tightened and the screw head and the rod are fixed simultaneously.

As shown in FIG. 2 by means of the arrows B the torque acting on the legs is more uniformly distributed so that a diagonal splaying of the legs can be almost fully prevented.

Figure 4A:
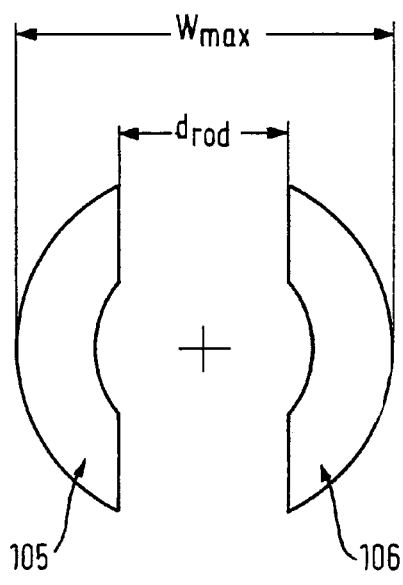
FIGS. 4a and 4b show schematically the principle of providing a stiffening structure according to the first embodiment of the receiving part.
Figure 4B:
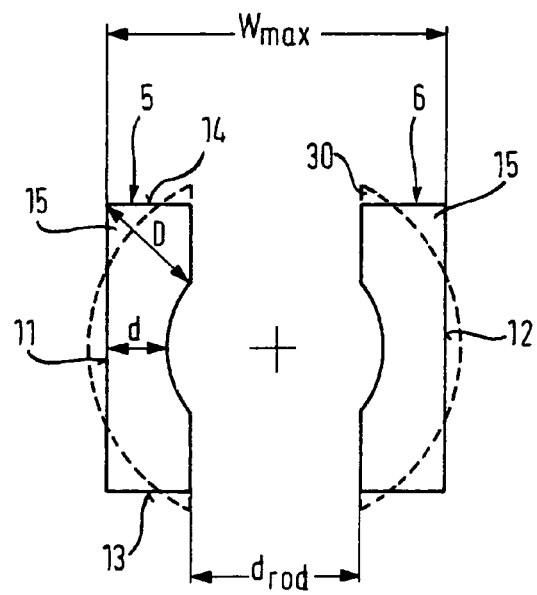

FIGS. 4a and 4b schematically show the principle of enhancing the stiffness of the legs 5, 6 according to the invention. In the conventional receiving part shown in FIG. 4a the legs have a cross-section in a direction transverse to the central axis M shaped like the shape of a section of a cylinder. Flattening the outer wall of the legs in a direction parallel to the longitudinal axis L of the recess 4 to generate the flat surfaces 11, 12 diminishes the wall thickness to a value d at a position closest to the central axis M. The thickness d is smaller than the wall thickness in the region of the lateral edges of the legs. Further flattening the surfaces perpendicular to the longitudinal axis L of the recess 4 to create the flat surfaces 13, 14 eliminates the sharp edges 30 and generates portions 15 with enhanced wall thickness D at the lateral edges of the legs. This provides a stiffening structure to prevent diagonal splaying of the legs. The following example illustrates the effect achieved with the receiving part according to the invention. By using a rod with a diameter $d_{rod}$ of 5.5 mm and with an inner diameter of 7 mm of the inner threaded portion, the lateral width $W_{max}$ of the receiving part according to the invention in a direction transverse to the rod is reduced to 11.5 mm compared to 13 mm in the conventional receiving part. The geometrical moment of inertia which is a measure for the stiffness of the flanks, is enhanced to 380 $mm^4$ for the receiving part according to the invention compared to 240 $mm^4$ in the conventional case.

The reduced lateral width $W_{max}$ allows the construction of more anatomically shaped lower sides of the bone anchoring devices which contributes to reducing the load on and/or the contact with the facet joints.

On the contrary, if a receiving part according to the invention has the same lateral width $W_{max}$ as the conventional cylindrical receiving part, the receiving part according to the invention can have a larger recess 4 for the use of a rod with a larger diameter without decreased stiffness.

The receiving part 1 may be produced by providing a cylindrical part and producing the flat surfaces by milling.

The invention is not limited to the use of the receiving part in a bone anchoring device as shown in FIGS. 3a and 3b. Other polyaxial connections are possible, for example the head and the rod may be fixed separately. In this case separate rod fixation means and head fixation means are provided. Further, in the embodiment shown the screw head and the tapering section are of a spherical shape, but any other shape is possible as long as the head of the bone anchoring screw and the tapering section function as a ball and socket joint. For example, the tapering section can be conically shaped.

The invention is further not limited to polyaxial bone anchoring devices but is also applicable to monoaxial bone anchoring devices. In this case, the second end 3 of the receiving part is fixedly connected to a shank which is to be anchored in a bone.

The shank can be a threaded shank as shown in the Figures but may also be a pin or a hook or another device which is apt to be anchored in the bone.

The inner thread can have any shape, although a shape which reduces the forces directed radially outward is preferred.

Figure 5A:
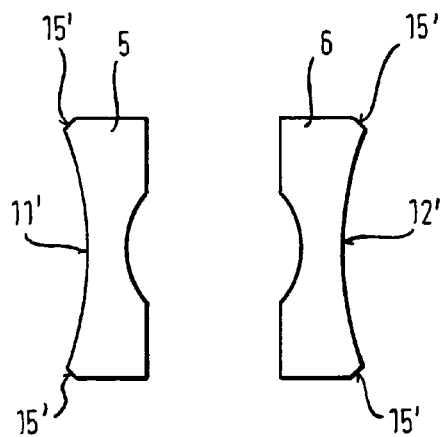
FIG. 5a shows a schematic view of the cross section of the open legs of a receiving part according to a second embodiment of the invention.
Figure 5B:
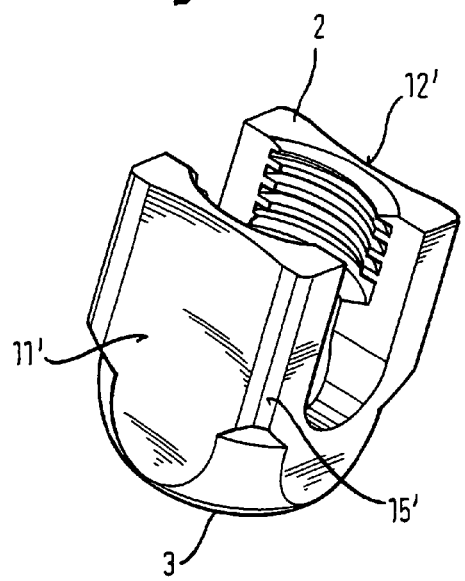
FIG. 5b shows a perspective view of the receiving part according to the second embodiment.

A second embodiment of the receiving part is shown in FIGS. 5a and 5b. The second embodiment differs from the first embodiment shown in FIGS. 1 to 3b in that the surfaces 11', 12' corresponding to the flat surfaces 11, 12 are not flat but concavely shaped and that the portions 15' having an enhanced wall thickness which are the outer edges of the concave surfaces 11', 12' extend along the whole length of legs up to the first end 2. Although stiffness is reduced compared to the first embodiment, the splaying of the legs is still considerably reduced with the receiving part of the second embodiment. The receiving part of the second embodiment has the advantage that the concave surfaces facilitate gripping of the receiving part by the surgeon.

Figure 6A:
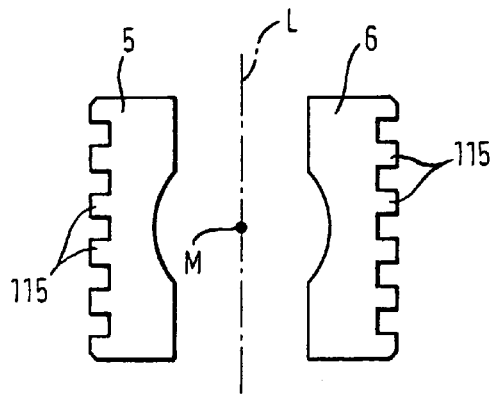
FIG. 6a shows a schematic view of the cross section of the open legs of a receiving part according to a third embodiment of the invention.
Figure 6B:
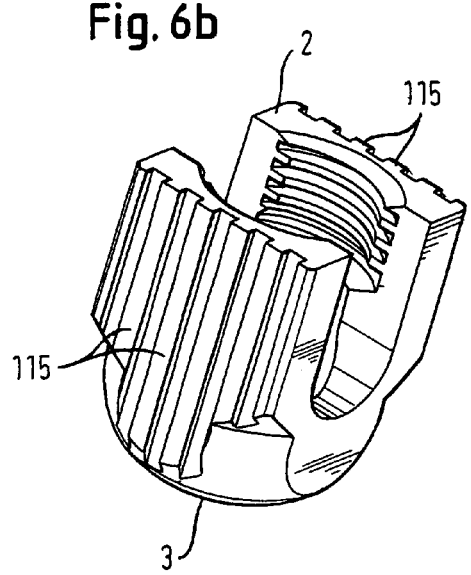
FIG. 6b shows a perspective view of the receiving part according to the third embodiment.

A third embodiment of the receiving part is shown in FIGS. 6a and 6b. The third embodiment differs from the first embodiment shown in FIGS. 1 to 3b in that the flat surfaces 11, 12 are provided with longitudinal ribs 115 extending in a direction transverse to the longitudinal axis L of the channel and parallel to the central axis M of the receiving part over the whole surface of the flat surfaces. The longitudinal ribs facilitate gripping of the receiving part.

Other modifications are possible. The ribs do not need to extend over the whole outer surface of the legs. Further, also the second embodiment may have such longitudinal ribs on the concave surfaces 11', 12'. It is even conceivable to provide the ribs at the outer surfaces of the conventional, convexly shaped outer surfaces of the known receiving parts.

In a further modification the stiffening structures are realized by adding to the basic material from which the receiving part is formed one or more additional materials to stiffen the basic material. This can be made, for example, by adding fibers, for example carbon fibers, or by adding glass beads.

Figure 7:
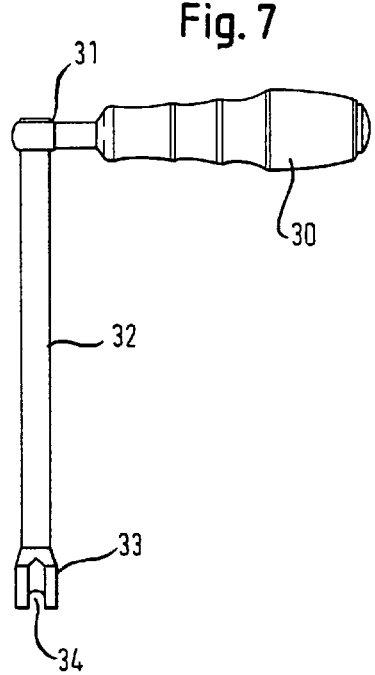
FIG. 7 shows a side view of a counter holding tool.

FIG. 7 shows a conventional counter-holding tool for use with receiving parts of polyaxial screws. The counter-holding tool has a grip portion 30, a hollow shaft 32 which allows a screwing-in tool to be guided through and a holding portion 33 which has a circular shape for use with the conventional cylindrical receiving parts. The holding portion has opposite slits 34 to fit over the rod which allow counter-holding of the receiving part when the inner screw is screwed in.

Figure 8:
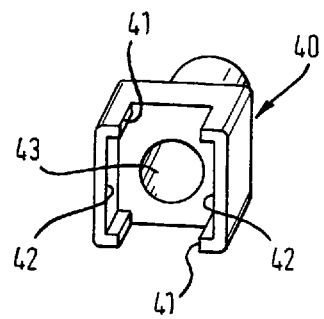
FIG. 8 shows a perspective view of a holding portion of a counter holding tool according to the invention.

According to the invention, the holding portion of the counter-holding tool is adapted to the shape of the receiving part. FIG. 8 shows the holding portion 40 for a counter-holding tool according to the invention. The holding portion 40 has a substantially square shaped contour with a hollow interior with an opening 43 which is connected to the hollow shaft of the counter-holding tool and two recesses 41 on opposite sides to fit onto the receiving part when the rod is inserted. The holding portion 40 further has two opposite parallel surfaces 42 which cooperate with the flat surfaces 11, 12 of the receiving part to provide a form-fit connection. The counter-holding tool is particularly suitable for percutaneous applications in minimally invasive surgery. By means of the form-fit connection between the holding portion and the receiving part it is possible to precisely align the receiving parts.

Figure 9:
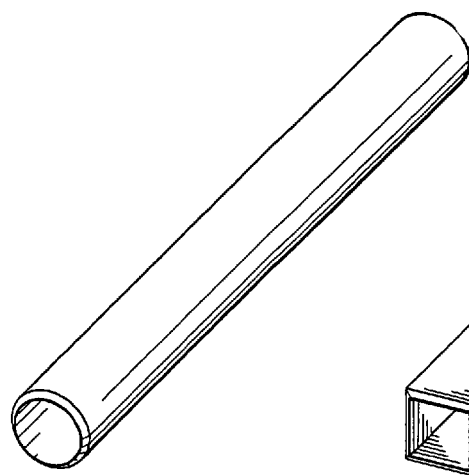
FIG. 9 shows a perspective view of a conventional trocar tool.
Figure 10:
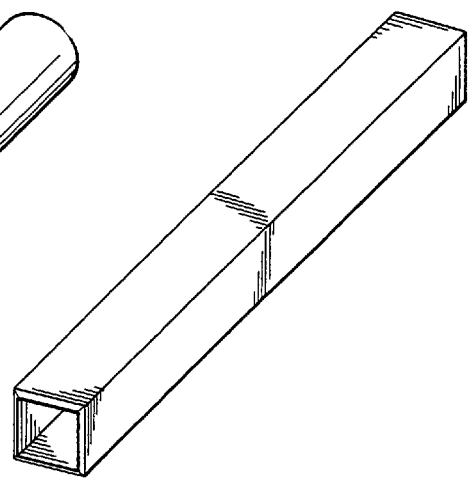
FIG. 10 shows a perspective view of a trocar tool according to the invention.
Figure 11:
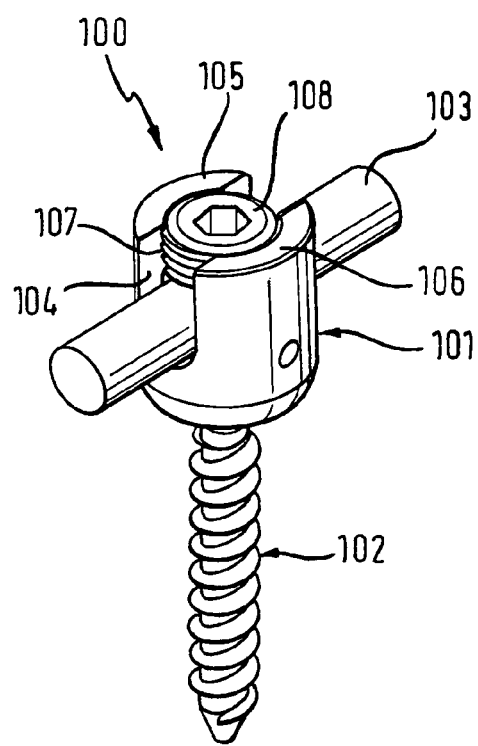
FIG. 11 shows a perspective view of a conventional polyaxial bone screw.
Figure 12:
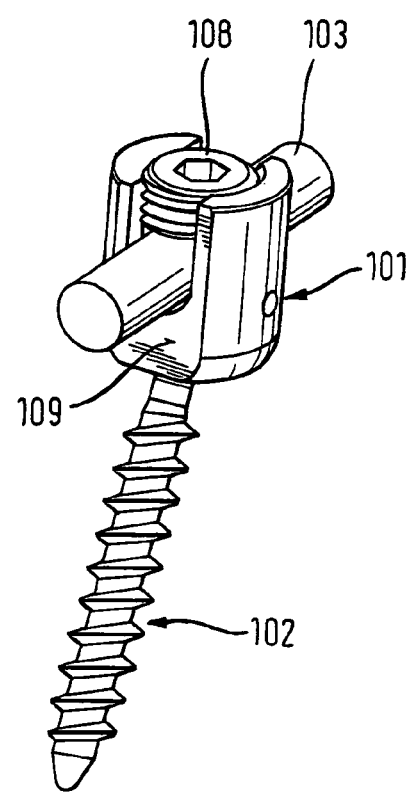
FIG. 12 shows a perspective view of a modified conventional polyaxial bone screw.
Figure 13:
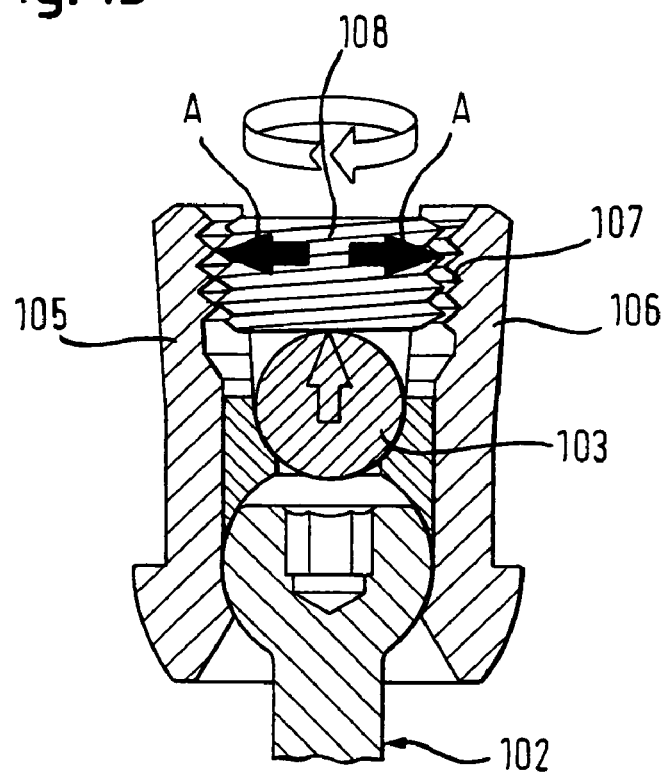
FIG. 13 shows a schematic sectional view illustrating a problem arising with the conventional receiving part.
Figure 14:
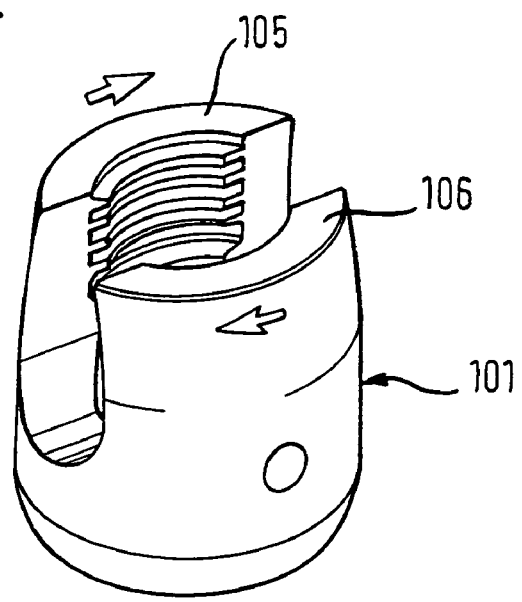
FIG. 14 shows a schematic view illustrating a further problem arising with the conventional receiving part.

FIG. 9 shows a conventional tube part of a trocar for minimally invasive surgery which has a circular cross-section. FIG. 10 shows a tube part of a trocar according to the invention which has a shape adapted to the shape of the receiving part which is substantially square. With the tube part according to FIG. 10, due to the form-fit connection between the receiving part and the tube part, it is possible, for example, to precisely introduce and align the bone anchoring device by means of percutaneous introduction.

What is claimed is:

1. A bone anchoring device comprising a bone anchoring element having a shank, a receiving part for connecting the shank of the bone anchoring element to a rod, and a securing element having an outer thread,
the receiving part comprising:
a first end and a second end and a central axis extending from the first end in a direction of the second end,
a recess having a substantially U-shaped cross section, the recess extending from the first end in the direction of the second end and forming two legs open at the first end and coming together at a bottom of the recess, the recess defining a channel to receive the rod, the channel having a longitudinal axis,
the two legs having an inner thread to receive the securing element, the outer thread configured to cooperate with the inner thread to secure the rod,
wherein the receiving part is polyaxially connectable to the bone anchoring element and the two legs are provided with stiffening structures to reduce splaying caused by a torque acting on the two legs at the time of final tightening of the rod by the securing element, the stiffening structures comprising a first envelope of the receiving part located above the bottom of the recess along a plane perpendicular to the central axis, the first envelope extending a greater distance from the central axis than every envelope of the receiving part that is parallel to the first envelope and located below the bottom of the recess.

2. The bone anchoring device of claim 1, wherein the stiffening structures are formed at an outer wall of the two legs.

3. The bone anchoring device of claim 2, wherein the stiffening structures comprise opposite flat surfaces, each of the surfaces formed in a respective outer wall of a leg of the two legs, the surfaces being parallel to the longitudinal axis of the channel.

4. The bone anchoring device of claim 3, wherein the flat surfaces extend from above the bottom of the recess to below the bottom of the recess.

5. The bone anchoring device of claim 3, wherein opposite flat surfaces are provided on sides of the receiving part perpendicular to the longitudinal axis of the channel.

6. The bone anchoring device of claim 4, wherein the flat surfaces extend substantially up to the first end.

7. The bone anchoring device of claim 1, wherein opposite flat surfaces are provided on sides of the receiving part perpendicular to the longitudinal axis of the channel.

8. The bone anchoring device of claim 1, wherein the first envelope of the receiving part is substantially square shaped.

9. The bone anchoring device of claim 1, wherein the stiffening structures are rib-like sections of enhanced wall thickness.

10. The bone anchoring device of claim 9, wherein the rib-like sections extend substantially in a direction of the first end to the second end.

11. The bone anchoring device of claim 9, wherein the stiffening structures are provided at a location so as to enclose an inserted rod from both sides.

12. The bone anchoring device of claim 10, wherein the stiffening structures are provided at a location so as to enclose an inserted rod from both sides.

13. The bone anchoring device of claim 1, wherein lateral edges of the legs comprise a section of enhanced material thickness.

14. The bone anchoring device of claim 1, the receiving part further having a bore extending from the first end to the second end for passing through the shank of the bone anchoring element.

15. The bone anchoring device of claim 14, wherein the receiving part further comprises a pressure element that is slidable in the bore for exerting pressure on a head of the bone anchoring element to fix the bone anchoring element at an angular position with respect to the receiving part.

16. The bone anchoring device of claim 15, wherein the stiffening structures are formed by an enhanced wall thickness of the legs located at a height of a longitudinal axis of a rod inserted in the receiving part.

17. The bone anchoring device of claim 16, wherein the enhanced wall thickness of the legs diminishes towards the first end of the receiving part.

18. The bone anchoring device of claim 1, wherein the stiffening structures are formed by the wall thickness of outer edges of the legs being larger than a wall thickness of the legs at a location between the outer edges of the legs, the outer edges spaced from each other in the direction of the longitudinal axis.

19. The bone anchoring device of claim 1, wherein the stiffening structures comprise additional material to stiffen a base material of the legs.

20. The bone anchoring device of claim 19, wherein the additional material is located only in a portion of the legs.

21. A bone anchoring kit, comprising a bone anchoring element having a shank, a receiving part for connecting the shank of the bone anchoring element to a rod, a securing element having an outer thread, and a tool having a tubular holding portion having a non-circular shape configured to receive the receiving part,
the receiving part comprising:
a first end and a second end and a central axis extending from the first end in a direction of the second end,
a recess having a substantially U-shaped cross section, the recess extending from the first end in a direction of the second end and forming two legs open at the first end and coming together at a bottom of the recess, the recess defining a channel between the legs to receive the rod, the channel having a longitudinal axis,
the two legs having an inner thread to receive the securing element, the inner thread on each of the two legs extending uninterrupted along substantially the full width of each leg, the outer thread configured to engage and cooperate with the inner thread to permit the securing element to contact and secure the rod,
wherein the receiving part is polyaxially connectable to the bone anchoring element and the two legs are provided with stiffening structures,
wherein the stiffening structures comprise a first envelope of the receiving part located above the bottom of the recess along a plane perpendicular to the central axis, the first envelope extending a greater distance from the central axis than every envelope of the receiving part that is parallel to the first envelope and located below the bottom of the recess.

22. A bone anchoring device comprising a bone anchoring element having a shank, a rod, a receiving part for connecting the shank of the bone anchoring element to the rod, and a securing element having an outer thread,
the receiving part comprising:
a first end and a second end and a central axis extending from the first end in a direction of the second end,
a recess having a substantially U-shaped cross section, the recess extending from the first end in the direction of the second end and forming two legs open at the first end and coming together at a bottom of the recess, the recess defining a channel to receive the rod, the channel having a longitudinal axis,
the two legs having an inner thread to receive the securing element, the outer thread configured to cooperate with the inner thread to secure the rod,
wherein the receiving part is polyaxially connectable to the bone anchoring element and the two legs are provided with stiffening structures to reduce splaying caused by a torque acting on the two legs at the time of final tightening of the rod by the securing element,
wherein along a first plane perpendicular to the central axis and including a longitudinal axis of a rod received in the channel, the receiving part has a first thickness along a first radial direction from the central axis and a second thickness along a second radial direction from the central axis, the first thickness being greater than the second thickness to form the stiffening structures, and
wherein along a second plane parallel to the first plane and positioned closer to the first end, the receiving part has a third thickness in the first radial direction that is less than the first thickness while maintaining the second thickness in the second radial direction.

23. A bone anchoring device comprising a bone anchoring element having a shank, a receiving part for connecting the shank of the bone anchoring element to a rod, and a securing element having an outer thread,
the receiving part comprising:
a first end and a second end and a central axis extending from the first end in a direction of the second end,
a recess having a substantially U-shaped cross section, the recess extending from the first end in the direction of the second end and forming two legs open at the first end and coming together at a bottom of the recess, the recess defining a channel to receive the rod, the channel having a longitudinal axis,
the two legs having an inner thread to receive the securing element, the outer thread configured to cooperate with the inner thread to secure the rod,
wherein the receiving part is polyaxially connectable to the bone anchoring element and the two legs are provided with stiffening structures to reduce splaying caused by a torque acting on the two legs at the time of final tightening of the rod by the securing element, such that along at least one plane perpendicular to the longitudinal axis of the channel, a cross-section of the receiving part includes a portion above the bottom of the recess having a greatest width in a direction perpendicular to the central axis that is greater than a width of any portion of the cross-section below the bottom of the recess.

* * * * *

UNITED STATES PATENT AND TRADEMARK OFFICE
CERTIFICATE OF CORRECTION

| | |
|---|---|
| PATENT NO. | : 8,262,704 B2 |
| APPLICATION NO. | : 11/440489 |
| DATED | : September 11, 2012 |
| INVENTOR(S) | : Wilfried Matthis et al. |

It is certified that error appears in the above-identified patent and that said Letters Patent is hereby corrected as shown below:

On the Title Page

(75) Inventors       Delete "VS-Fillingen (DE)"
                     Insert -- VS-Villingen (DE) --

Signed and Sealed this
Eighteenth Day of June, 2013

Teresa Stanek Rea
*Acting Director of the United States Patent and Trademark Office*